(12) United States Patent
Kaufhold et al.

(10) Patent No.: US 6,674,835 B2
(45) Date of Patent: Jan. 6, 2004

(54) METHODS AND APPARATUS FOR ESTIMATING A MATERIAL COMPOSITION OF AN IMAGED OBJECT

(75) Inventors: John Patrick Kaufhold, Altamont, NY (US); Jeffrey Wayne Eberhard, Albany, NY (US); Dinko E. Gonzalez Trotter, Clifton Park, NY (US); Bernhard Erich Hermann Claus, Niskayuna, NY (US); John Eric Tkaczyk, Delanson, NY (US)

(73) Assignee: General Electric Co., Schenectady, NY (US)

( * ) Notice: Subject to any disclaimer, the term of this patent is extended or adjusted under 35 U.S.C. 154(b) by 266 days.

(21) Appl. No.: 09/976,693

(22) Filed: Oct. 12, 2001

(65) Prior Publication Data

US 2003/0072409 A1 Apr. 17, 2003

(51) Int. Cl.$^7$ .............................................. G01N 23/06
(52) U.S. Cl. ............................ 378/53; 378/56; 378/207
(58) Field of Search .......................... 378/207, 51, 53, 378/511, 56, 18

(56) References Cited

U.S. PATENT DOCUMENTS

| | | | |
|---|---|---|---|
| 5,537,485 | A | 7/1996 | Nishikawa et al. |
| 5,821,541 | A | 10/1998 | Tumer |
| 5,844,965 | A | 12/1998 | Galkin |
| 5,881,127 | A | 3/1999 | Molloi et al. |
| 6,052,433 | A | 4/2000 | Chao |
| 6,134,297 | A | 10/2000 | Chao |
| 6,173,034 | B1 | 1/2001 | Chao |
| 6,230,045 | B1 | 5/2001 | Hoogenraad et al. |

*Primary Examiner*—Harshad Patel
(74) *Attorney, Agent, or Firm*—Armstrong Teasdale LLP; Robert B. Reeser, III (57) ABSTRACT

A method for estimating a material composition of an imaged object using an imaging system. The imaging system includes a radiation source and a digital detector. The method also includes scanning a plurality of calibration phantoms with varying material composition to acquire a plurality of reference calibration images, estimating an attenuation coefficient thickness product for each pixel in the reference calibration images, and estimating a material composition of a region of interest using the estimated pixelwise coefficient thickness product.

30 Claims, 5 Drawing Sheets

FIG. 3 cm of 100F (green*s). cm of 50/50 (blue x's). cm of 100G (black o's)

Plot of $y_{phantom}$ versus phantom thickness

Plot of $P_O$ versus effective attenuation coefficient.

FIG. 6 measured radiological thickness versus $G_c$

FIG. 7

METHODS AND APPARATUS FOR ESTIMATING A MATERIAL COMPOSITION OF AN IMAGED OBJECT

BACKGROUND OF THE INVENTION

This invention relates generally to imaging systems, and more particularly, to calibration of a medical imaging system.

In at least some known imaging systems, a radiation source projects a cone-shaped beam which passes through the object being imaged, such as a patient and impinges upon an array of radiation detectors. In some known tomosynthesis systems, the radiation source rotates with a gantry around a pivot point, and views of the object are acquired for different projection angles. As used herein "view" refers to a single projection image or, more particularly, "view" refers to a single projection radiograph which forms a projection image. Also, as used herein, a single reconstructed (cross-sectional) image, representative of the structures within the imaged object at a fixed height above the detector, is referred to as a "slice". And a collection (or plurality) of views is referred to as a "projection dataset." A collection of (or a plurality of) slices for all heights is referred to as a "three-dimensional dataset" representative of an imaged object.

One known method of reconstructing a three-dimensional dataset representative of an imaged object is known in the art as simple backprojection, or shift-and-add. Simple backprojection backprojects each view across the imaged volume, and averages the backprojected views. A "slice" of the reconstructed dataset includes the average of the back-projected images for some considered height above the detector. Each slice is representative of the structures of the imaged object at the considered height, and the collection of these slices for different heights, constitutes a three-dimensional dataset representative of the imaged object. Alternatively, in a two-dimensional scan, such as, for example, a Cranio-caudal scan (CC scan) or a mediolateral-oblique scan (MLO), only a single slice is acquired constituting a two-dimensional dataset representative of the imaged object.

In at least one known imaging system, highly attenuating regions of a breast appear brighter than less attenuating regions of the breast. However, deriving a mathematical relationship between specific tissue composition and each individual detector pixel's photon count is usually complicated by the physics of the imaging chain. Due to these complications, a quantitative tissue composition measurement, although theoretically possible, is rarely performed in mainstream medicine.

BRIEF DESCRIPTION OF THE INVENTION

A method for estimating a material composition of an imaged object using an imaging system is provided. The imaging system includes a radiation source and a digital detector. The method also includes scanning a plurality of calibration phantoms with varying material composition to acquire a plurality of reference calibration images, estimating an attenuation coefficient thickness product for each pixel in the reference calibration images and estimating a material composition of a region of interest using the estimated pixelwise coefficient thickness product.

A medical imaging system for estimating a material composition of an imaged object is provided. The medical imaging system includes a radiation source and a digital detector, and a computer coupled to the radiation source and the digital detector. The computer is configured to scan a plurality of calibration phantoms with varying material composition to acquire a plurality of reference calibration images, estimate an attenuation coefficient thickness product for each pixel in the reference calibration images, and estimate a material composition of a region of interest using the estimated coefficient thickness product.

A computer readable medium encoded with a program executable by a computer for estimating a material composition of an imaged object is provided. The program is configured to instruct the computer to scan a plurality of calibration phantoms with varying material composition to acquire a plurality of reference calibration images, estimate an attenuation coefficient thickness product for each pixel in the reference calibration images, and estimate a material composition of a region of interest using the estimated coefficient thickness product.

DETAILED DESCRIPTION OF THE INVENTION

Figure 1:
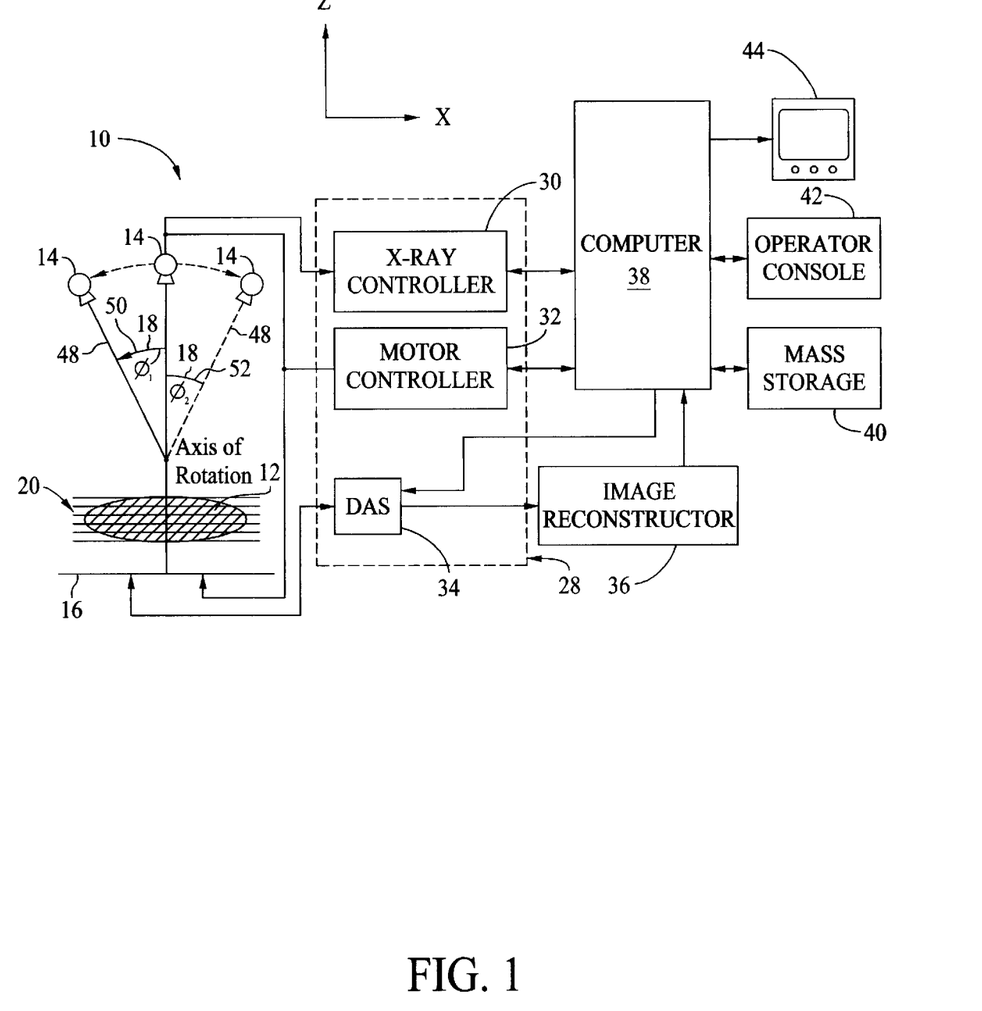
FIG. 1 is a block schematic diagram of a digital imaging system.

Referring to FIG. 1 and in an exemplary embodiment, a digital imaging system 10 generates a three-dimensional dataset representative of an imaged object 12, such as a patient's breast 12 in mammographic tomosynthesis. System 10 includes a radiation source 14, such as an x-ray source 14, and at least one detector array 16 for collecting views from a plurality of projection angles 18. Specifically and in one embodiment, system 10 includes a radiation source 14 which projects a cone-shaped beam of x-rays which pass through object 12 and impinge on detector array 16. The views obtained at each angle 18 can be used to reconstruct a plurality of slices, i.e., images representative of structures located in planes 20 parallel to detector 16. Detector array 16 is fabricated in a panel configuration having a plurality of pixels (not shown) arranged in rows and columns so that an image is generated for an entire object of interest such as breast 12. In one embodiment, detector array 16 is a cardiac detector array 16 and object 12 is a heart 12. Additionally, although herein described in a three-dimensional application, it is contemplated that the benefits of the invention accrue to all scanning applications including two-dimensional applications.

Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces an electronic signal that represents the intensity, after attenuation by object 12, of an x-ray beam impinging on detector array 16. In one embodiment, detector array 16 is approximately 20 cm by 20 cm and is configured to produce views for an entire object of interest, e.g., breast 12. Alternatively, detector array 16 is variably sized depending on the intended use. Additionally, the individual pixels on detector array 16 can also be any size depending on the intended use.

In another embodiment, alternative detector technology is used, such that views in digital form are generated by detector 16. In one embodiment, the reconstructed three-dimensional dataset is not arranged in slices corresponding to planes that are parallel to detector 16, but in a more general fashion. In another embodiment, the reconstructed dataset consists only of a single two-dimensional image, or a one-dimensional function. In yet another embodiment, detector 16 is other than planar or other than rectangular.

In one embodiment, radiation source 14 and detector array 16 are moveable relative to object 12 and each other. More specifically, radiation source 14 and detector array 16 are translatable so that projection angle 18 of the imaged volume is altered. Radiation source 14 and detector array 16 are translatable such that projection angle 18 may be any acute or oblique projection angle.

The operation of radiation source 14 is governed by a control mechanism 28 of imaging system 10. Control mechanism 28 includes a radiation controller 30 that provides power and timing signals to radiation source 14 and a motor controller 32 that controls the respective translation speed and position of radiation source 14 and detector array 16. A data acquisition system (DAS) 34 in control mechanism 28 samples digital data from detector 16 for subsequent processing. An image reconstructor 36 receives sampled and digitized projection dataset from DAS 34 and performs high speed image reconstruction, as described herein. The reconstructed three-dimensional dataset, representative of imaged object 12, is applied as an input to a computer 38 which stores the three-dimensional dataset in a storage device 40 such as a hard drive, a compact disk (CD) drive, and/or a DVD. Image reconstructor 36 is programmed to perform functions described herein, and, as used herein, the term image reconstructor refers to computers, processors, microcontrollers, microcomputers, programmable logic controllers, application specific integrated circuits, and other programmable circuits.

Computer 38 also receives commands and scanning parameters from an operator via console 42 that has an input device. A display 44, such as a cathode ray tube and/or a liquid crystal display (LCD) allows the operator to observe the reconstructed three-dimensional dataset and other data from computer 38. The operator supplied commands and parameters are used by computer 38 to provide control signals and information to DAS 34, motor controller 32, and radiation controller 30.

In use, a patient is positioned so that the object of interest 12 is within the field of view of system 10, i.e., breast 12 is positioned within the imaged volume extending between radiation source 14 and detector array 16. Views of breast 12, are then acquired from at least two projection angles 18 to generate a projection dataset of the volume of interest. The plurality of views represent the tomosynthesis projection dataset. The collected projection dataset is then utilized to generate a three-dimensional dataset, i.e., a plurality of slices for scanned breast 12, representative of the three-dimensional radiographic representation of imaged breast 12. After enabling radiation source 14 so that the radiation beam is emitted at first projection angle 50, a view is collected using detector array 16. Projection angle 18 of system 10 is then altered by translating the position of source 14 so that central axis 48 of the radiation beam is altered to a second projection angle 52 and position of detector array 16 is altered so that breast 12 remains within the field of view of system 10. Radiation source 14 is again enabled and a view is collected for second projection angle 52. The same procedure is then repeated for any number of subsequent projection angles 18.

Figure 2:
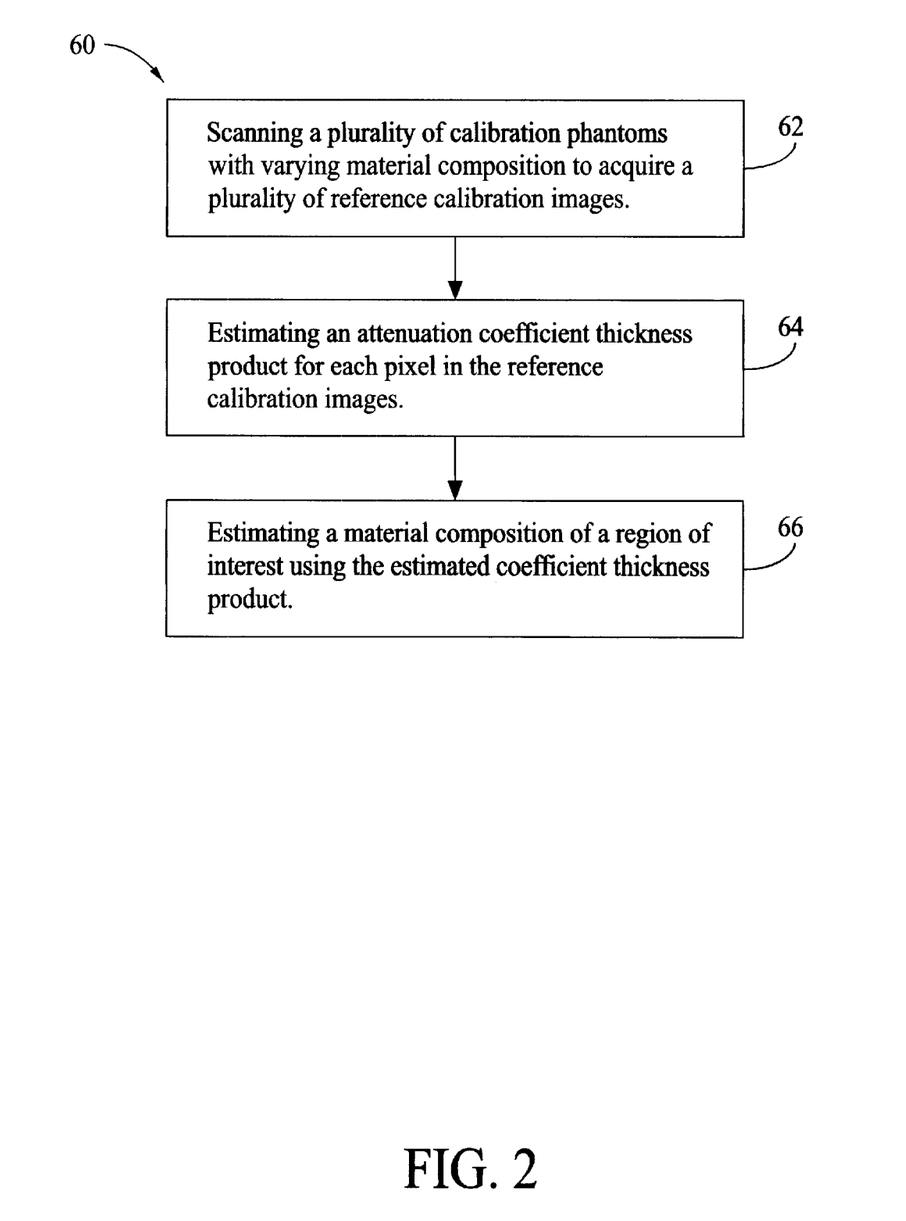
FIG. 2 is flow diagram of a method for estimating a material composition of an imaged object.

FIG. 3 is a flow diagram of a method 60 including estimating a material composition of an imaged object 12 (shown in FIG. 1) using an imaging system 10 (shown in FIG. 1). Method 60 also includes scanning 62 a plurality of calibration phantoms 100 with varying material compositions to acquire a plurality of reference calibration images, estimating 64 an attenuation coefficient thickness product for each pixel in the reference calibration images, and estimating 66 a material composition of a region of interest (ROI) using the estimated pixelwise coefficient thickness products.

Figure 3:
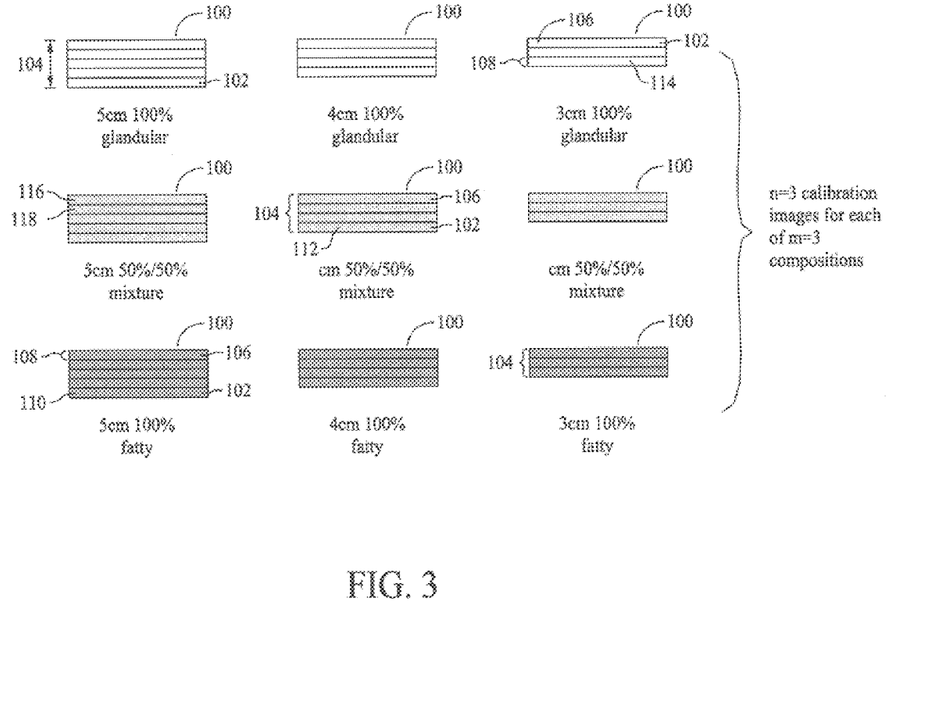
FIG. 3 is side view of a plurality of calibration phantoms.

FIG. 3 is a side view of a plurality of calibration phantoms 100. Calibration phantom 100 includes a plurality of slabs 102 and thicknesses 104. Slab 102 includes a plurality of varying material compositions 106, such as breast equivalent material 106, and a slab thickness 108. Breast equivalent material 106 includes, but is not limited to a 100% fat-equivalent material 110, a 50% fat/50% glandular-equivalent material 112, and a 100% glandular-equivalent material 114. In another embodiment, material composition 106 is not a breast equivalent material and slabs 102 are utilized in applications other than breast imaging applications. Slabs 102 are arranged such that at least one first slab 116 extends over at least one second slab 118.

In one embodiment, a plurality of calibration phantoms 100 are used to calibrate digital detector 18 for radiation source 14 which is capable of producing x-ray spectra which include, but are not limited to, a 26 kV 100 mAs Rhodium filtered beam from a Rhodium anode. In one embodiment, calibration phantom 100 includes four slabs 102 including 100% fat-equivalent material 110, wherein each slab 102 is one centimeter (cm) thick, therefore calibration phantom thickness 104 is four cm. Alternatively, the quantity of slabs 102, phantom thickness 104, breast equivalent material 106, and slab thickness 108 are variably selected depending on the compressed breast thickness H cm to be imaged. A plurality of slab thicknesses 108 are used to generate multiple points in the thickness-log photon count domain. Alternatively, to predict photon count data from other neighboring calibration phantom thicknesses 104, by interpolation or extrapolation, the information from neighboring phantom thicknesses 104 may be used.

In use, scanning 62 a plurality of calibration phantoms 100 with varying material compositions includes placing a plurality of calibration phantoms 100 in approximately the same position on detector 14 as breast 12 will be placed when breast 12 is imaged. A plurality of phantoms 100 including a plurality of phantom slabs 102 are stacked to each of n different thicknesses 104 given a specified compressed breast thickness (H cm) and scanned 62 to generate calibration data which includes an intensity value measurement for each pixel. In an exemplary embodiment, the intensity value relates to the photon counts. In one embodiment, where n=3, three calibration phantoms 100 are scanned 62 including a first calibration phantom 100 including three slabs 102, a second calibration phantom 100 including four slabs 102, and a third calibration phantom 100 including five slabs 102, wherein each calibration phantom 100 includes a different breast equivalent material 104. For each material (m) 106, n images are scanned, for a total of m×n reference images to calibrate each radiation source 14 configuration, and calibration phantom 100 and thicknesses 104. The specific heights about H cm, do not have to be equally spaced, do not have to be the same for each of the n measurements, or include the height H cm, as one of the imaged heights. At least one calibration phantom 100, including thickness 104, or a plurality of calibration phantoms 100, including a plurality of phantom thicknesses 104, may be imaged depending on beam-hardening effects and the confidence interval on the attenuation coefficient estimation for each composition as described herein.

In one embodiment, the measured photon counts, i.e. pixel intensity, for each reference calibration image are adjusted to normalize out a plurality of imaging error conditions, such as, but not limited to, correcting for scattered x-ray radiation, x-ray pathlength variation on the image due to geometric effects, x-ray filter thickness variation, and electronic drift in detector 16. The photon intensity characterizes the total amount of x-ray beam attenuation from radiation source 14 to a detector pixel and is used to generate a plurality of radiological thickness measurements of known reference calibration materials 106 and thicknesses 104.

In use, a plurality of scatter-corrected and gain-corrected reference calibration images are generated using the previously determined photon counts at each pixel in the calibration data. In one embodiment, the reference images are corrected. Reference image correction includes removing the effects of electronic drift in digital detector 16 over time, geometric effects ($r^2$ effects), and non-uniform detector counting characteristics which are spatially varying over digital detector 16 are removed using the measured or modeled photon counts. For tomosynthesis and standard view projection mammogram applications, the reference images can be gain corrected, i.e. removing any angle-dependent variations inherent in tomographic and standard view scanning protocols. The radiation incident on detector 16 that originated from x-ray source 14 is either "primary" or "scattered". This means that each x-ray photon can either pass through the material directly and not scatter (herein referred to as "primary"), or it can deflect off of some nuclei and scatter at least once (herein referred to as "scattered"). The scattered radiation is estimated and removed from the reference calibration images using a scatter-correction algorithm. In one embodiment, the scatter-correction algorithm includes a plurality of modulation factors which account for scattered radiation path-lengths that contribute to the scatter kernel. Scatter radiation estimation and correction facilitates removing, from the reference calibration images, only the contributions to the photon counts that are introduced from sources other than the reference calibration phantom. Photon counts due to primary x-ray events passing through the calibration phantoms are not removed.

Estimating 64 an attenuation coefficient thickness product for each pixel in the reference calibration images includes transforming a plurality of photon counts to a measure that is linear in the attenuation coefficient thickness product. The attenuation coefficient thickness product characterizes the total amount of x-ray beam attenuation from the radiation source 14 to the detector pixel. In use, a negative natural log of each pixel in the scatter-corrected and gain-corrected reference calibration images is calculated according to:

$$y_{phantom}(i, j) = -\log(I_{phantom}(i, j)) \quad \text{Equation 1}$$

where $y_{phantom}(i, j)$ is a scaled and shifted measure of the attenuation coefficient-thickness product estimate, i and j are pixel indices, and "log" indicates the natural log. The $y_{phantom}(i, j)$ is a scaled and shifted version of the attenuation coefficient-thickness product because it can be expressed as a linear function of $\mu$T where $\mu$ is the attenuation coefficient of material 106 and T is thickness 104 of phantom 100.

Estimating 66 a material composition of a ROI using the estimated coefficient thickness product of an object 12 (shown in FIG. 1) includes using each pixel's photon count and the compressed breast thickness to create a calibration curve and an analytic expression for an estimate of tissue composition. In one embodiment, a method for estimating a composition of a ROI includes a model-based estimation using a theoretical model of $I_{phantom}(i, j)$ which represents the photon count for a plurality of pixels at location i and j.

In use, a plurality of reference calibration images are used to estimate a plurality of constants in a model. Each reference image pixel photon count on detector 18 can be approximated by:

$$y_{phantom}(i, j) = \int_{energy} P_0(E, x, y) \exp\left(\int_{pathlength} -\mu_{phantom}(E, x, y, x) dp\right) dE \quad \text{Equation 2}$$

where $P_0(E, x, y)$ is an x-ray dependent quantity of attenuation-free counts for each $\mu(E)$, and $\mu(E, x, y)$ is the x-ray energy-dependent attenuation coefficient of breast 12 at each position on digital detector 16. Further, the integrals over pathlength describe the trajectories of the individual x-ray beams to each pixel location, and the integral over energy indicates that pixel intensity is due to a poly-energetic spectrum of x-rays. Using a mono-energetic approximation to the poly-energetic x-ray beam attenuation model, and recognizing that the attenuation coefficient is constant for each calibration phantom in Equation 2, a calibration phantom pixel mono-energetic approximation to the intensity model for a plurality of photon counts $I_{phantom}(i, j)$ is:

$$I_{phantom}(i, j) = P_0(\mu_{phantom}) e^{-\mu_{phantom} T_{phantom}} \quad \text{Equation 3}$$

where $\mu_{phantom}$ is the attenuation coefficient of each reference calibration phantom, $T_{phantom}$ is the thickness 104 of each reference calibration phantom 100, and a polyenergetic spectrum ($P_0$) can be expressed as a function of the attenuation coefficient of each phantom material composition 106 to account for beam-hardening effects.

Given the mono-energetic approximation to the intensity model for the photon counts, the attenuation coefficient can be expressed in terms of the photon counts as:

$$\mu_{phantom} = \frac{\log(P_0(\mu_{phantom})) - y_{phantom}(i, j)}{T_{phantom}} \quad \text{Equation 4}$$

In one embodiment, the linear attenuation coefficient can be estimated using the slope of the $y_{phantom}$ values versus phantom thickness 104, i.e. $T_{phantom}$ 104. To estimate the breast tissue-equivalent attenuation coefficients for glandular tissue $\mu_G$ and fatty tissue $\mu_F$, and the $P_0$ spectrum for each $\mu$ of interest, best-fit lines to $y_{phantom}$ versus $T_{phantom}$ 104 can be used.

Figure 4:
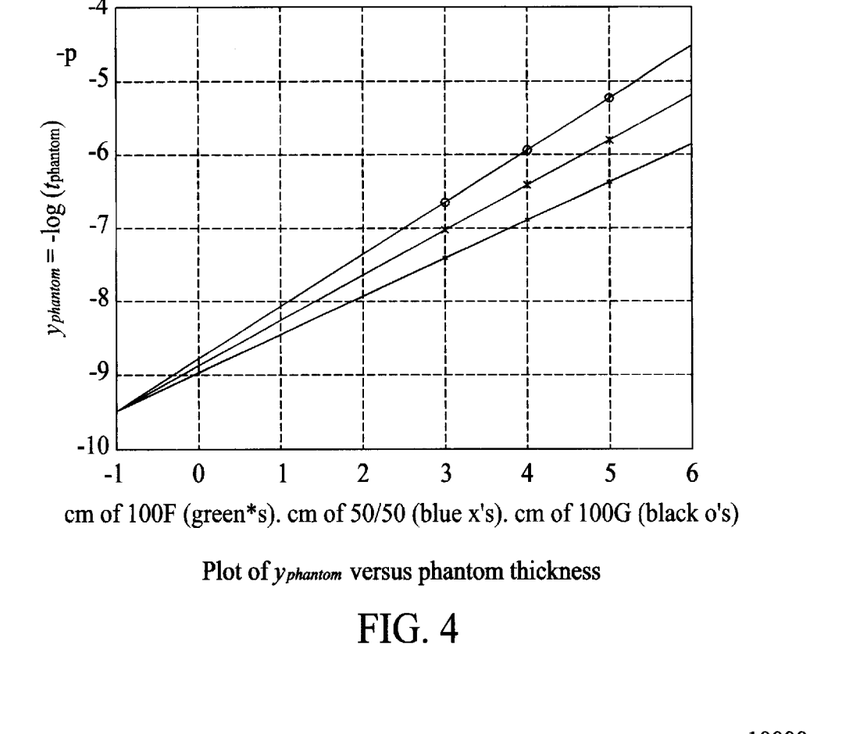
FIG. 4 is a plot of the negative natural logarithm of the photon counts versus phantom thickness for a plurality of calibration phantoms including a plurality of materials.

FIG. 4 is a plot of the negative natural logarithm of the photon counts versus phantom thickness for a plurality of calibration phantoms, including a thickness 104 of four cm, and including a plurality of materials acquired with an x-ray beam produced by a Rhodium anode at 26 kV and 100 mAs further filtered by Rhodium.

Figure 5:
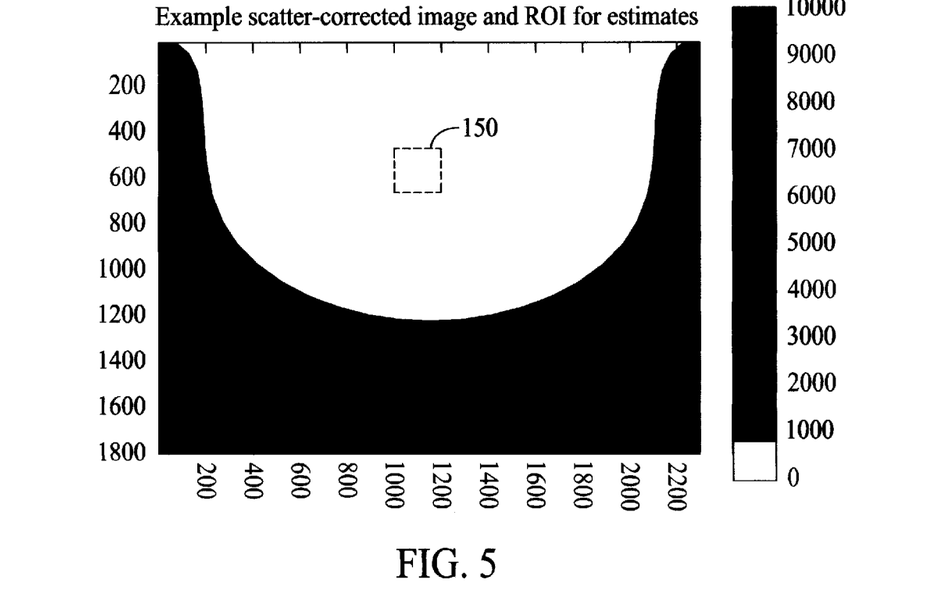
FIG. 5 is a calibration reference image from which an ROI can be selected.

FIG. 5 is a calibration reference image 150 from which an ROI can be selected. The plot in FIG. 4 is generated by choosing a ROI far from the edges of the calibration phantom 100 to further eliminate effects due to residual scatter. For example, box 150 is a ROI for a typical reference calibration phantom 100. Referring again to FIG. 4, the mean of the negative log of the intensity values of pixels in each ROI was used for each thickness. Alternatively a plurality of other representative metrics can be used. In one embodiment, a scalar or vector representation of the pixels in the ROI (the mean or median, e.g.) can be used in the estimation of attenuation coefficients. Alternatively, the best-fit lines can be estimated using the data for a given nominal reference phantom calibration image, depending on noise or other measurement considerations. The best-fit lines for three different calibration phantoms 100, including different materials 106 and different phantom thicknesses 104 are shown in FIG. 4. Due to beam-hardening and other effects, there may be some systematic bending or other variation from linearity in the plots of $Y_{phantom}$ versus $T_{phantom}$ 104. The quantity of acquisitions of different thicknesses 104 for the same composition 106 can be increased or decreased for attenuation coefficient estimation based on the variability in the measurements and the error bars on the best-fit line to the data. In another embodiment, a thickness resolution of calibration measurements can be adjusted to be larger or smaller. For example, using the best-fit lines in FIG. 4, the y-intercept is used to estimate $P_0$ for each reference calibration phantom material 106. A relationship between an effective $P_0$ and material 106 can be established from a set of $P_0$ estimates for a suitable number of reference calibration phantom images.

Figure 6:
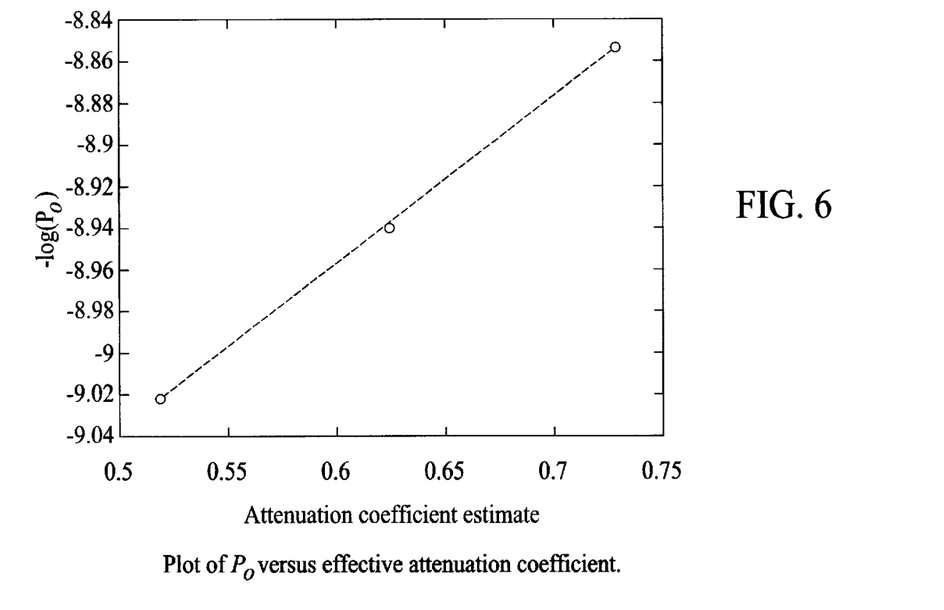
FIG. 6 is a graphical representation of the y-intercepts of the physical quantities extracted from the plot shown in FIG. 4.

FIG. 6 is graphical representation of the y-intercepts of the physical quantities extracted from the plot shown in FIG. 4. Negative $\log(P_0)$ is plotted in FIG. 6 as a function of $\mu$ using the example data in FIG. 4. In one embodiment, $\log(P_0)$ is a linear function of a percent glandular material, where the higher $P_0$ values correspond to less attenuating materials.

In one embodiment, $P_0$ can be estimated as a function of an effective attenuation coefficient, $\mu_{eff}$, of a calibration phantom 100 using a parametric curve-fit to the data as shown in FIG. 6. In another embodiment, $P_0$ estimation can be accomplished using a first-principles approach to estimating the relationship by using quantities related to the theoretical models for x-ray properties, including material composition 106, the physics of the detector photon counting and/or scintillator device, or a direct conversion device.

In one embodiment, a nominal variation in $\log(P_0)$ is small over the attenuation coefficient estimates of interest and, as such, the nominal variation can be regarded as constant, and the effective attenuation coefficient of an unknown sample can be estimated as:

$$\mu_{eff} = \frac{\log(P_0) - y_{sample}}{T_{sample}} \qquad \text{Equation 5}$$

Because both $P_0$ and the effective attenuation coefficient depend on the sample, an iterate for $\mu_{eff}$ can be written:

$$\mu_{eff}^{i+1} = \frac{\log(P_0(\mu_{eff}^i)) y_{sample}}{T_{sample}} \qquad \text{Equation 6}$$

where the superscript i indicates the iteration number.

For materials relevant to breast composition determination, Equation 6 can be initialized using:

$$\mu_{eff}^0 = \frac{\mu_{gland} + \mu_{fat}}{2} \qquad \text{Equation 7}$$

alternatively, any initialization in the region of convergence for the iterate can be used. In one embodiment, Equation 6 can be iterated until there is little change from iteration to iteration of either $\mu_{eff}$ or $P_0(\mu_{eff})$ to estimate the effective attenuation coefficient of an unknown sample. In another embodiment, material composition 106 is not a breast equivalent material and an initialization is done in applications other than breast imaging applications.

The effective attenuation coefficient estimates $\mu_{gland}$, $\mu_{fat}$, and $P_0(\mu_{eff})$ are used to derive an equation for material composition as a function of photon counts. Using the mono-energetic equation in terms of an unknown $G_c$, (percent glandular tissue in a phantom or breast image of unknown composition) and unknown $F_c$ (percent fatty tissue in a phantom or breast image of unknown composition), $G_c$ can be written as:

$$G_c = 100 \frac{(\log(P_0(\mu_{eff})) - y_{measured} - \mu_{fat} H)}{H(\mu_{gland} - \mu_{fat})} \qquad \text{Equation 8}$$

and $F_c$ can similarly be written as:

$$F_c = 100 \frac{(\log(P_0(\mu_{eff})) - y_{measured} - \mu_{gland} H)}{H(\mu_{fat} - \mu_{gland})} \qquad \text{Equation 9}$$

In one embodiment, all the variables on the right hand sides in Equations 5 and 6 are known using estimates from the calibration data and the measured or otherwise determined thickness 104 of the sample.

Figure 7:
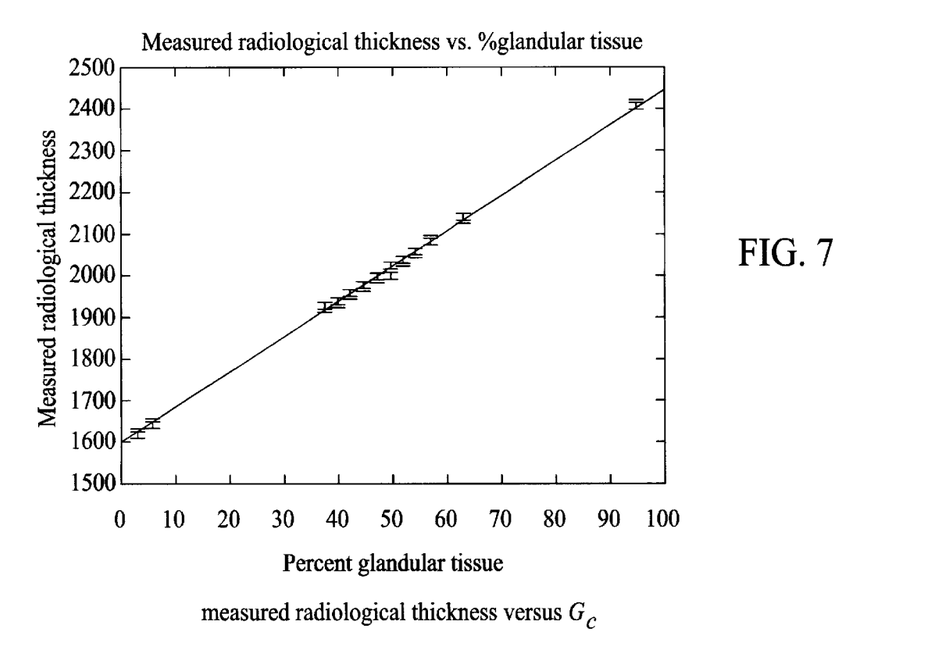
FIG. 7 is a graphical representation of an alternative embodiment for estimating $G_c$ and $F_c$ using a graphical method.

FIG. 7 is a graphical representation of an alternative embodiment for estimating $G_c$ and $F_c$ using a graphical method. In one embodiment, $G_c$ for m phantom compositions can be plotted as a function of $y_{phantom}$ as illustrated in FIG. 7. Note that the y axis on FIG. 7 is not exactly $-\log(\text{counts})$, they range in the thousands. This is because that y axis is in a related domain, not simply $-\log(\text{counts})$. Specifically, the y axis on FIG. 7 is a constant plus a constant times the negative $\log(\text{counts})$. $G_c$ for a thickness 102 can be estimated using a parametric fit of $G_c$ ($y_{phantom}$) for any given sample of the same compressed thickness. $F_c$ can be estimated as $100 - G_c$.

In another embodiment, a direct empirical approach is used to estimate tissue composition from the calibration data without a theoretical model based on the physics of the imaging chain. Additionally, hybrid methods are also possible. In alternative embodiment, a graphical method is used which, while empirical in nature, does not require the modeling of the above described approach with attenuation coefficients. In one graphical method, the patient data is directly compared to a similar calibration curve.

A patient is scanned, subsequent to creating a calibration curve and an analytic expression for an estimate of tissue composition, to generate an image of object 22. In one embodiment, the exact image acquisition parameters for both the patient and reference calibration phantoms 100 need not match exactly. In one embodiment, the estimates from the calibration data are used in the equation for calculating percent glandular and percent fatty tissue, i.e. Equation 6, is used to estimate the constants in Equations 8 and 9. Alternatively, for the parametric fit method using $G_c$ ($y_{phantom}$) a similar curve-fit can be determined from the calibration data. If a different system other than system 10 is used to image the patient, a machine-dependent adjustment can be made to map the constants computed for use in Equation 4 to their corresponding values on the different image system. In one embodiment, the compressed breast thickness, H cm, is recorded from the compression unit. Alternatively, H cm can be estimated using a plurality of projections of small lead markers. In another alternative embodiment, an external device can be used to measure compressed breast thickness H cm.

The patient data is normalized, in the same way that the reference calibration phantoms data is normalized to remove effects introduced by the physics of the imaging chain. In use, the photon count data from the patient breast image is gain-corrected and scatter-corrected according to: $I_{sample}(i,j)$ where i and j are pixel indices.

The patient data is transformed into the same measure of radiological thickness (in one domain, the Y-axis of FIG. 7) as the reference calibration phantom data set described herein such that the patient data is converted to a domain appropriate to the specific calibration method (parametric, empirical, or hybrid). In use, the photon counts at each sample pixel are transformed according to their corresponding $y_{sample}$ values according to:

$$y_{sample}(i, j) = -log(I_{sample}(i, j)) \quad \text{Equation 10}$$

In one embodiment, the analytic expression or calibration curve described previously herein is used to estimate the percent tissue composition of pixels in the patient image. Equations 7, 8 and 9, as described herein, are used to calculate the percent glandular and percent fat for patient breast 12 at each pixel within the compressed region of the breast. Alternatively, Equations 7, 8, and 9 can be applied to pixels outside the compressed region of the breast by modifying the scatter-estimation.

In another embodiment, using the previous $G_c$ fit to the $y_{phantom}$ values, $G_c$ is estimated for the breast sample by computing $G_c(y_{sample})$. $F_c$ is computed according to $F_c = 100 - G_c$.

While the invention has been described in terms of various specific embodiments, those skilled in the art will recognize that the invention can be practiced with modification within the spirit and scope of the claims.

What is claimed is:

1. A method for estimating a material composition of an imaged object using an imaging system, the imaging system including a radiation source and a digital detector, said method comprising:
scanning a plurality of calibration phantoms with varying material composition to acquire a plurality of reference calibration images;
estimating an attenuation coefficient thickness product for each pixel in the reference calibration images; and
estimating a material composition of a region of interest using the estimated pixelwise coefficient thickness product.

2. A method in accordance with claim 1 wherein the varying material compositions include a plurality of breast-equivalent materials.

3. A method in accordance with claim 1 wherein estimating a material composition of an imaged object further comprises adjusting the reference calibration images to to generate a plurality of scatter-corrected and gain-corrected images.

4. A method in accordance with claim 3 wherein adjusting the reference calibration images comprises normalizing out a plurality of imaging error conditions.

5. A method in accordance with claim 4 wherein normalizing out a plurality of imaging conditions include correcting the reference calibration images to remove the effects of scatter, electronic drift in the detector, geometric effects, and non-uniform detector counting characteristics.

6. A method in accordance with claim 1 wherein estimating an attenuation coefficient thickness product for each pixel in the reference calibration images includes transforming a plurality of photon counts to a measure that is linear in the attenuation coefficient thickness product.

7. A method in accordance with claim 6 wherein transforming a plurality of photon counts to a measure that is linear in the attenuation coefficient thickness product includes transforming in accordance with $y_{phantom}(i, j) = -log(I_{phantom}(i, j))$.

8. A method in accordance with claim 1 wherein to estimate a composition of a region of interest of an object further comprises estimating a composition of a region of interest using a model-based estimation including a theoretical model.

9. A method in accordance with claim 1 wherein the region of interest of an object is a region of interest of a breast.

10. A method for estimating a material composition of an imaged object using an imaging system, the imaging system including a radiation source and a digital detector, said method comprising:
scanning a plurality of calibration phantoms comprising a plurality of breast-equivalent materials to acquire a plurality of reference calibration images;
estimating an attenuation coefficient thickness product for each pixel in the reference calibration images comprises transforming a plurality of photon counts to a measure that is linear in the attenuation coefficient in accordance with $y_{phantom}(i, j) = -log(I_{phantom}(i, j))$ and wherein estimating an attenuation coefficient further comprises adjusting the reference calibration images to remove the effects of scatter, electronic drift in the detector, geometric effects, and non-uniform detector counting characteristics generate a plurality of scatter-corrected and gain corrected images; and
estimating a material composition of a region of interest using the estimated coefficient thickness product.

11. A medical imaging system for estimating a material composition of an imaged object, said medical imaging system comprising:
a detector array;
at least one radiation source; and
a computer coupled to said detector array and radiation source and configured to:

scan a plurality of calibration phantoms comprising varying material composition to acquire a plurality of reference calibration images;

estimate an attenuation coefficient thickness product for each pixel in the reference calibration images; and estimate a material composition of a region of interest using the estimated coefficient thickness product.

12. A medical imaging system in accordance with claim 11 wherein to scan a plurality of calibration phantoms comprising varying material compositions, said computer further configured to scan a plurality of calibration phantoms comprising a plurality of breast-equivalent materials.

13. A medical imaging system in accordance with claim 11 wherein to estimate a material composition of an imaged object, said computer further configured to adjust the reference calibration images to generate a plurality of scatter-corrected and gain corrected images.

14. A medical imaging system in accordance with claim 13 wherein to adjust the reference calibration images, said computer further configured to normalize out a plurality of imaging error conditions.

15. A medical imaging system in accordance with claim 14 wherein to normalize out a plurality of imaging conditions, said computer further configured to remove the effects of scatter, electronic drift in the detector, geometric effects, and non-uniform detector counting characteristics.

16. A medical imaging system in accordance with claim 11 wherein to estimate an attenuation coefficient thickness product for each pixel in the reference calibration images, said computer further configured to transform a plurality of photon counts to a measure that is linear in the attenuation coefficient thickness product.

17. A medical imaging system in accordance with claim 16 wherein to transform a plurality of photon counts to a measure that is linear in the attenuation coefficient thickness product, said computer further configured to transform in accordance with $y_{phantom}(i, j) = -\log(I_{phantom}(i, j))$.

18. A medical imaging system in accordance with claim 11 wherein to estimate a composition of a region of interest of an object, said computer further configured to estimate a composition of a region of interest using a model-based estimation including a theoretical model.

19. A medical imaging system in accordance with claim 11 wherein to estimate a composition of a region of interest of an object, said computer further configured to estimate a composition of a region of interest of a breast.

20. A medical imaging system for estimating a material composition of an imaged object, said medical imaging system comprising:

a detector array;

at least one radiation source; and a computer coupled to said detector array and radiation source and configured to:

scan a plurality of calibration phantoms comprising a plurality of breast-equivalent materials to acquire a plurality of reference calibration images;

estimate an attenuation coefficient thickness product for each pixel in the reference calibration images, wherein to estimate an attenuation coefficient thickness product further comprises transforming a plurality of photon counts to a measure that is linear in the attenuation coefficient in accordance with $y_{phantom}(i, j) = -\log(I_{phantom}(i, j))$ and adjusting the reference calibration images to remove the effects of scatter, electronic drift in the detector, geometric effects, and non-uniform detector counting characteristics generate a plurality of scatter-corrected and gain corrected images; and estimate a material composition of a region of interest using the estimated coefficient thickness product.

21. A computer readable medium encoded with a program executable by a computer for reconstructing a three-dimensional dataset representative of an imaged object, said program configured to instruct the computer to:

scan a plurality of calibration phantoms comprising varying material composition to acquire a plurality of reference calibration images;

estimate an attenuation coefficient thickness product for each pixel in the reference calibration images; and estimate a material composition of a region of interest using the estimated coefficient thickness product.

22. A computer readable medium in with claim 21 wherein to scan a plurality of calibration phantoms comprising varying material compositions, said program further configured to scan a plurality of calibration phantoms comprising a plurality of breast-equivalent materials.

23. A computer readable medium in accordance with claim 21 wherein to estimate a material composition of an imaged object, said program further configured to adjust the reference calibration images to generate a plurality of scatter-corrected and gain corrected images.

24. A computer readable medium in accordance with claim 23 wherein to adjust the reference calibration images, said program further configured to normalize out a plurality of imaging error conditions.

25. A computer readable medium in accordance with claim 24 wherein to normalize out a plurality of imaging conditions, said program further configured to remove the effects of scatter, electronic drift in the detector, geometric effects, and non-uniform detector counting characteristics.

26. A computer readable medium in accordance with claim 21 wherein to estimate an attenuation coefficient thickness product for each pixel in the reference calibration images, said program further configured to transform a plurality of photon counts to a measure that is linear in the attenuation coefficient thickness product.

27. A computer readable medium in accordance with claim 26 wherein to transform a plurality of photon counts to a measure that is linear in the attenuation coefficient thickness product, said program further configured to transform in accordance with $y_{phantom}(i, j) = -\log(I_{phantom}(i, j))$.

28. A computer readable medium in accordance with claim 21 wherein to estimate a composition of a region of interest of an object, said program further configured to estimate a composition of a region of interest using a model-based estimation including a theoretical model.

29. A computer readable medium in accordance with claim 21 wherein to estimate a composition of a region of interest of an object, said program further configured to estimate a composition of a region of interest of a breast.

30. A computer readable medium encoded with a program executable by a computer for reconstructing a three-dimensional dataset representative of an imaged object, said program configured to instruct the computer to:

scan a plurality of calibration phantoms comprising a plurality of breast-equivalent materials to acquire a plurality of reference calibration images;

estimate an attenuation coefficient thickness product for each pixel in the reference calibration images, wherein to estimate an attenuation coefficient thickness product further comprises transforming a plurality of photon counts to a measure that is linear in the attenuation coefficient in accordance with $y_{phantom}(i, j) = -\log(I_{phantom}(i, j))$ and adjusting the reference calibration images to remove the effects of scatter, electronic drift in the detector, geometric effects, and non-uniform detector counting characteristics generate a plurality of scatter-corrected and gain corrected images; and estimate a material composition of a region of interest using the estimated coefficient thickness product.

* * * * *

UNITED STATES PATENT AND TRADEMARK OFFICE
CERTIFICATE OF CORRECTION

PATENT NO. : 6,674,835 B2  Page 1 of 1
DATED : January 6, 2004
INVENTOR(S) : John Patrick Daufhold et al.

It is certified that error appears in the above-identified patent and that said Letters Patent is hereby corrected as shown below:

Column 1,
Line 5, insert:
-- STATEMENT REGARDING FEDERALLY SPONSORED RESEARCH & DEVELOPMENT      The US Government may have certain rights in this invention pursuant to Contract No. MDA905-00-1-0041 awarded by the Henry M. Jackson Fundation For The Advancement Of Military Medicine.

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,674,835 B2 |
| APPLICATION NO. | : 09/976693 |
| DATED | : January 6, 2004 |
| INVENTOR(S) | : John Patrick Kaufhold et al. |

It is certified that error appears in the above-identified patent and that said Letters Patent is hereby corrected as shown below:

<u>Title page,</u>
Item [75], Inventors, "Daufhold" should read -- Kaufhold --.

Signed and Sealed this

Twenty-seventh Day of June, 2006

JON W. DUDAS
*Director of the United States Patent and Trademark Office*